United States Patent [19]

Tanaka

[11] Patent Number: 5,300,963
[45] Date of Patent: Apr. 5, 1994

[54] STRUCTURE FOR ATTACHING MEMBER FOR PROTECTING EYES FROM WIND AND DUST

[75] Inventor: Haruka Tanaka, Yao, Japan

[73] Assignee: Kanda Optical Co., Ltd., Japan

[21] Appl. No.: 14,831

[22] Filed: Feb. 8, 1993

[30] Foreign Application Priority Data

Feb. 14, 1992 [JP] Japan .................................. 4-79406

[51] Int. Cl.[5] ............................................. G02C 7/10
[52] U.S. Cl. ....................................... 351/44; 351/41; 2/426
[58] Field of Search ...................... 351/44, 45, 47, 41, 351/111, 121; 2/426, 431

[56] References Cited

U.S. PATENT DOCUMENTS 1,516,261  5/1923  Youngquist .............................. 2/431
3,384,903  5/1968  Malcom, Jr. ............................ 351/44
4,630,321  12/1986  Sagemuehl et al. ..................... 2/426

FOREIGN PATENT DOCUMENTS 2605754  4/1988  France ................................. 351/44

OTHER PUBLICATIONS

Catalog, "I Ski/Suncloud 87/88", I Ski/Suncloud, Los Angeles, CA, Copyright 1987, pp. 14, 15 and Cover.

Primary Examiner—William L. Sikes
Assistant Examiner—Hung Xuan Dang
Attorney, Agent, or Firm—Pravel, Hewitt, Kimball & Krieger

[57] ABSTRACT

An eye protecting hood member made of a soft material is joined to lens rims and auxiliary temples of a spectacle frame made of a rigid material, without using any adhesive. The hood member is provided in the form of a fin between an upper side of each rim and the auxiliary temple and between an outer lateral side of each rim and the auxiliary temple for closing a space between the hood member and the face of the wearer. The lens rim is formed in the inner face of each of the upper side and the outer lateral side with at least one narrow groove so shaped as to enlarge toward its bottom. Each of the temples is formed in its inner face with at least one narrow groove so shaped as to enlarge toward its bottom. The soft material forming the hood member is filled in the narrow grooves in the lens rim and the auxiliary temple. Preferably, the narrow groove of the lens rim has a channel communicating with a lens fitting groove, and the auxiliary temple has a bore vertically extending therethrough. The soft material forming the hood member is also filled in the channel and the bore.

8 Claims, 3 Drawing Sheets

STRUCTURE FOR ATTACHING MEMBER FOR PROTECTING EYES FROM WIND AND DUST

FIELD OF THE INVENTION

The present invention relates to an eye protecting device which comprises sunglasses or other spectacles and a member attached to the spectacles for protecting the eyes, for example, from the wind and dust.

BACKGROUND OF THE INVENTION

Goggles and the like are widely used in practicing active outdoor sports such as skiing and driving motorcycles which are movable at considerably high speeds to prevent the eyeballs from direct exposure to the wind and protect the eyes from dust particles suspending in the air.

Further in work factories wherein dust is produced, workers are under an obligation to wear dust-tight protective goggles for preventing dust particles from entering the eyes.

Goggles are widely known which have windshield and dust-tight functions and which comprise an eye protecting hood projecting from lens rims and a thick spongelike cushioning member affixed to the peripheral edge portion of the hood to be brought into contact with the face of the wearer. However, these goggles are bulky and therefore inconvenient to carry about, feel awkward when worn and are actually not in prevalent use except for skiers.

Accordingly, heretofore preferred are eye protecting spectacles of simple construction which merely have an eye protecting hood member 4 inwardly projecting in the form of a fin from the upper sides 14, 14 and outer lateral sides 13, 13 of lens rims 8, 8 as shown in FIG. 6. Nevertheless, since the lens rims 8 and the hood member 4 are integrally molded of rigid synthetic resin, these spectacles have the likelihood of injuring the skin when the projecting end of the rigid hood member 4 is forced against the face around the orbits.

To overcome this drawback, spectacles are made available which comprise a fin-shaped hood member molded of soft synthetic resin and adhered to lens rims of rigid synthetic resin, but there is no suitable adhesive which is capable of perfectly bonding the two materials, i.e., soft synthetic resin and rigid synthetic resin, which are different in characteristics. For this reason, the spectacles are insufficient in bond strength and have the drawback of permitting separation of the hood member from the lens rim if subjected to a great impact during use.

Eye protecting spectacles are therefore proposed which have eye protecting members 4 made of soft leather as seen in FIG. 7. The proposed spectacles comprise hood attaching fins 41 inwardly projecting from specified portions of the upper side 14 and outer lateral side 13 of each lens rim 8, a synthetic leather member fastened to the fins with rivets 42 to form the hood member 4, and a strip 43 of the same synthetic leather as above fastened to the hood member 4 by a rivet 42 with a temple 22 held between the strip and the hood member. However, the eye protecting spectacles require much labor for cutting the synthetic leather and riveting the leather components, and therefore have the drawback of being very expensive to make.

In view of the foregoing drawbacks, we have developed an eye protecting device which comprises a spectacle frame of rigid synthetic resin and an eye protecting hood member made of a soft synthetic resin material and firmly joined to the frame in intimate contact therewith without using any adhesive.

SUMMARY OF THE INVENTION

The eye protecting device of the invention has a spectacle frame made of a rigid material and comprising a single lens rim or a pair of lens rims having an upper side, a lower side and outer lateral sides, and a pair of temples bent and projecting inward from the respective rim outer lateral sides; and an eye protecting hood member made of a soft flexible material and provided in the form of a fin between the rim upper side and each temple and between each rim outer lateral side and each temple for closing a space between the spectacle frame and the face of the wearer of the device, the lens rim or rims being formed in the inner face of each of the upper and outer lateral sides with at least one narrow groove so shaped as to enlarge toward its bottom, each of the temples being formed in its inner face with at least one narrow groove so shaped as to enlarge toward its bottom, the hood member being firmly joined to the lens rim or rims and the temples in intimate contact therewith by filling the narrow grooves in the lens rim or rims and the temples with the soft material forming the hood member.

Preferably, each of the narrow grooves formed in the lens rim has a channel communicating with a lens fitting groove and filled with the soft material forming the hood member.

More preferably, each of the temples is formed with a bore vertically extending therethrough and filled with the soft material forming the hood member.

DETAILED DESCRIPTION OF THE INVENTION

Figure 1:
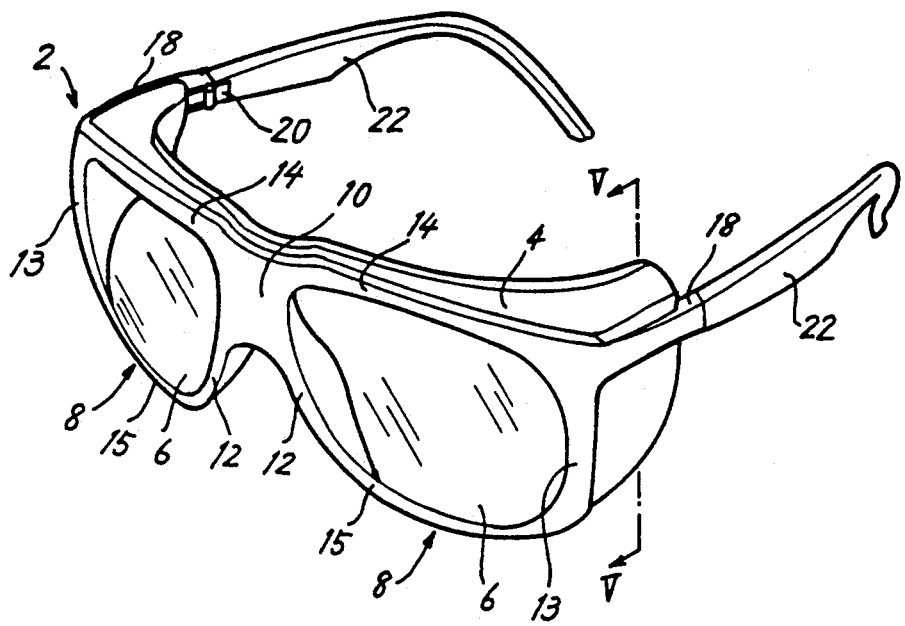
FIG. 1 is a perspective view of an eye protecting device embodying the invention and having an eye protecting hood member attached to a spectacle frame.

FIG. 1 is a view schematically showing an eye protecting device which comprises a spectacle frame 2 made of a rigid synthetic resin and an eye protecting hood member 4 made of a soft synthetic resin and attached to the spectacle frame 2.

The spectacle frame 2 comprises a pair of lens rims 8, 8 interconnected by a bridge 10 and each having an inner lateral side 12, outer lateral side 13, upper side 14 and lower side 15, auxiliary temples 18, 18 inwardly projecting from the outer lateral sides 13, 13 of the lens rims 8, 8 respectively and integral therewith, and main temples 22, 22 pivotably connected to the auxiliary temples 18, 18 by hinges 20, 20, respectively.

Each of the lens rims is formed with a lens fitting groove 16 (see FIG. 2), which has a lens 6 fitted therein.

The hood member 4, which is adapted to protect the eyes from the wind, dust and the like, is so shaped as to close a space between the spectacle frame 2 and is attached in the form of a fin to the upper sides 14, 14 and the outer lateral sides 13, 13 of the lens rims 8, 8 and the auxiliary temples 18, 18 as illustrated. Consideration should be given so as not to provide a sharp edge on a direct edge to the portion of the hood member 4 to be brought into contact with the face of the wearer.

The hood member is attached to the lens rims and the auxiliary temples by the structure to be described next in detail.

Figure 2:
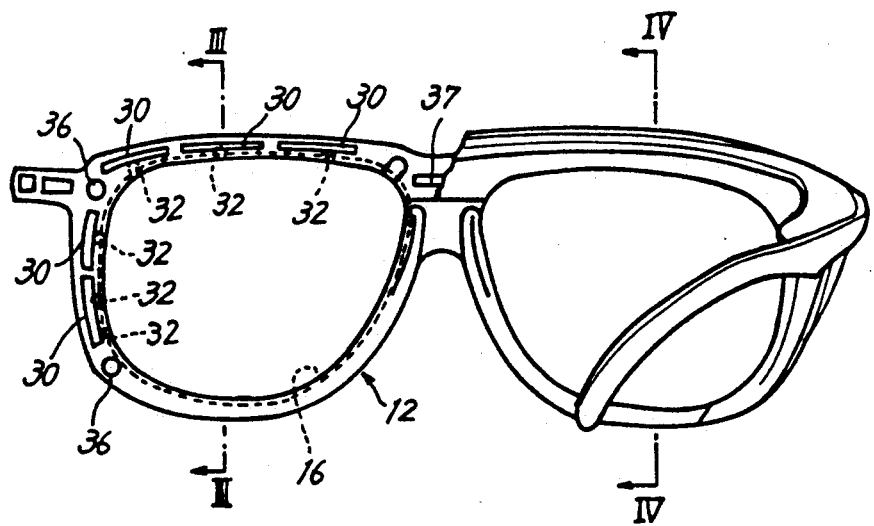
FIG. 2 is a diagram showing the eye protecting device of the invention as it is seen from inside thereof with the hood member partly removed.
Figure 3A:
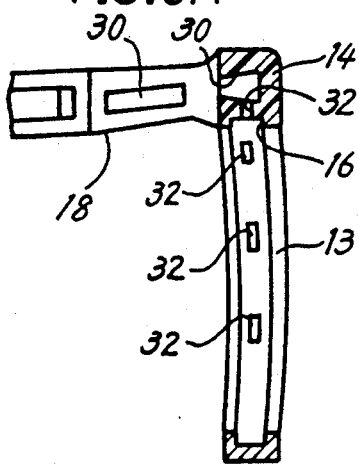
FIG. 3A is a view in section taken along the line III—III in FIG. 2.

As shown in FIG. 2, narrow grooves 30 arranged at a suitable spacing are formed in the inner faces of the upper side 14 and the outer lateral side 13 of each lens rim 8. Each narrow groove 30 is so shaped as to enlarge toward its bottom as seen in FIG. 3A.

Figure 3B:
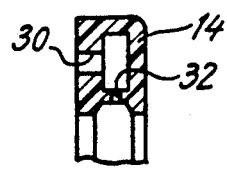
FIG. 3B is a view of a narrow groove having a modified form in cross section.

The narrow grooves 30 are enlarged toward the bottom and therefore will not permit the hood member to slip off the lens rims when filled with the soft resin material forming the hood member. The interior of the narrow groove need not always be limited to a so-called dovetail form continuously enlarging toward the bottom as shown in FIG. 3A but may be stepped to form an entirely enlarged interior space as shown in FIG. 3B.

The narrow grooves are formed at a suitable spacing to avoid a reduction in the strength of the lens rim 8. Accordingly, when the lens rim has a large thickness, such a discrete arrangement of grooves need not be formed but a single elongated narrow groove can be formed.

Preferably, the narrow groove 30 has a communicating channel 32 extending from the vicinity of its bottom to the lens fitting groove 16. When the soft resin material for forming the hood member is filled into the communicating channels the joint between the hood member and the lens rim can be given an increased strength to make the hood member less likely to slip off. Such communicating channels are formed preferably at a suitable spacing along the lens rim. Accordingly, long narrow grooves may have a plurality of communicating channels, while all short narrow grooves need not have such a channel.

As shown in FIG. 2, it is desirable to form a circular groove 36 or rectangular groove 37 in the lens rim as required at a portion thereof, such as a corner, where a relatively large area is available. These grooves are also shaped to have an enlarged interior portion like the narrow grooves 30 and filled with the soft resin material for forming the hood member.

As seen in FIG. 3A, the auxiliary temple 18 is also formed in its inner face with at least one narrow groove, which is also so shaped as to enlarge toward its bottom.

Figure 5A:
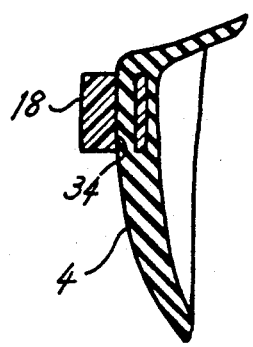
FIG. 5A is a view in section taken along the line V—V in FIG. 1.
Figure 5B:
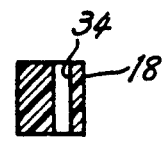
FIG. 5B is a view in cross section of the portion of an auxiliary temple including a bore extending therethrough.
Figure 6:
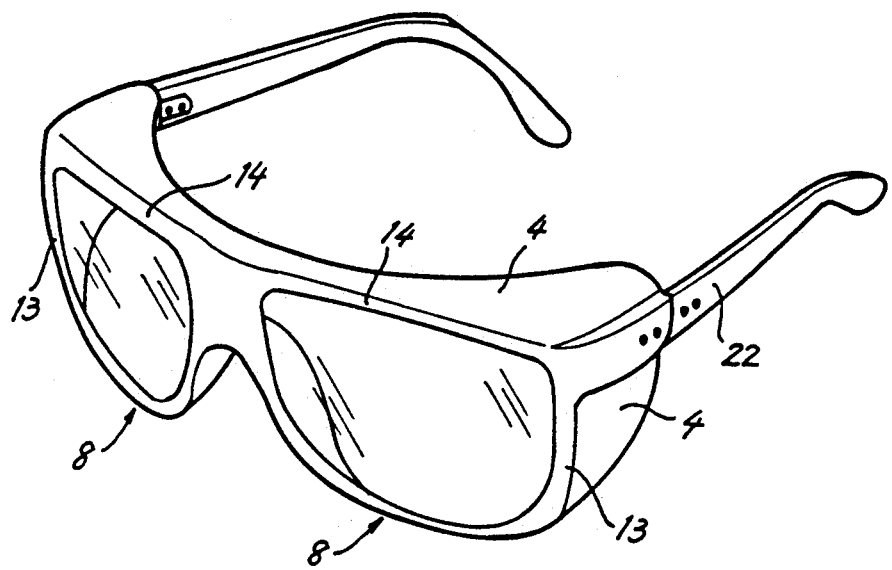
FIGS. 6 and 7 are perspective views showing conventional examples of eye protecting devices.
Figure 7:
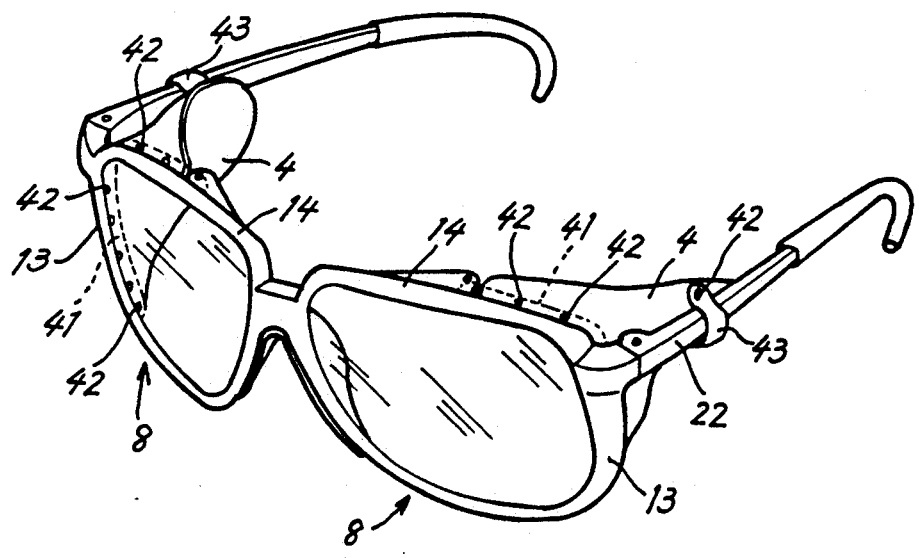

With reference to FIG. 5B, the auxiliary temple 18 preferably has a bore 34 vertically extending therethrough. The soft resin material for forming the hood member is filled into the bore 34 to give a higher strength to the joint between the hood member and the auxiliary temple and thereby make the hood member less likely to slip off.

The hood member is attached to the spectacle frame by the method to be described below.

The spectacle frame is molded as separated into a portion including the lens rims and the auxiliary temples, and the main temples.

The rigid resin material for forming the spectacle frame is, for example, 12 nylon resin having a melting point of about 200 to about 220° C. The soft resin material for forming the hood member is, for example, a polyamide resin, Elastomer PAE1200J-6 (product of Ube Industries, Japan), having a melting point of about 150 to about 160° C.

First, the portion including the lens rims and the auxiliary temples of the foregoing construction is prepared by a known molding process.

Figure 4:
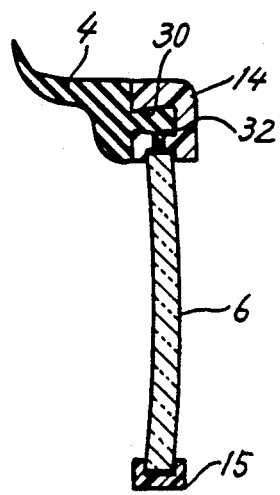
FIG. 4 is a view in section taken along the line IV—IV in FIG. 2.

Next, the resulting molding is placed into a mold for forming the hood member, and the soft material is placed into the mold and molded integrally with the molding. Consequently, the hood member of the desired shape is molded as joined to the above-mentioned portion, with the spaces of the narrow grooves 30, circular grooves 36 and rectangular groove 37 of the lens rims 8 filled with the soft resin material (see FIG. 4). Since the soft material molded later is about 40 to about 70° C. lower than the rigid material in melting point as previously stated, the rigid material previously molded will not melt.

In the case of the embodiment wherein the narrow grooves 30 have communicating channels 32, the molten soft material will flow out from the opening ends. To prevent this, the soft material is molded with a ring member, plate or like jig fitted in each lens fitting groove 16.

Since the soft material is molded as if holding the auxiliary temple 18 from above and below as seen in FIG. 5A, any additional jig need not be used even in the case of embodiment wherein the through bore 34 is formed.

Because the present device has the foregoing structure, the hood member can be firmly joined to the spectacle frame without using any adhesive. Furthermore, the hood member is made of soft resin material and is therefore unlikely to injure the face of the wearer.

Further because the hood member resembles a fin and is simple in construction, the device can be worn like conventional sunglasses. Moreover, the device can be rendered more fashionable when the hood member is made different from the spectacle frame in color.

The attaching structure for the hood member is not limited to use with the binocular spectacle frame of the foregoing embodiment but can of course be applied also to monocular spectacle frames. With reference to FIG. 1, the monocular spectacle frame need not have the inner lateral sides 12, 12 and the bridge 10 interconnecting these sides, includes the lower sides 15, 15 which are made continuous and has a single lens rim.

The auxiliary temples 18 need not always be provided but the main temples 22 may be made to project directly from the outer lateral sides of the respective lens rims.

The lenses mountable on the lens rim are a wide variety of lenses including prescription lenses, light blocking lenses for protecting the eye from ultraviolet rays, plain glass or plastics plates, etc.

The components of the present device are not limited to those of the foregoing embodiments in construction but can be modified variously by one skilled in the art without departing from the technical scope defined in the appended claims.

What is claimed is:

1. A device for protecting the eyes from wind and dust comprising:
   a single lens rim or a pair of lens rims made of a rigid material and having an upper side, a lower side and outer lateral sides,
   a pair of temples bent and projecting inward from the respective rim outer lateral sides, and
   an eye protecting hood member made of a soft flexible material and provided in the form of a fin between the rim upper side and each temple and between each rim outer lateral side and each temple for closing a space between the spectacle frame and the face of the wearer of the device,
   the lens rim or rims being formed in the inner face of each of the upper and outer lateral sides with at least one narrow groove so shaped as to enlarge toward its bottom,
   each of the temples being formed in its inner face with at least one narrow groove so shaped as to enlarge toward its bottom,
   the hood member being firmly joined to the lens rim or rims and the temples in intimate contact therewith by filling the narrow grooves in the lens rim or rims and the temples with the soft material forming the hood member.

2. An eye protecting device as defined in claim 1 wherein the narrow groove formed in the lens rim has a channel communicating with a lens fitting groove and filled with the soft material forming the hood member.

3. An eye protecting device as defined in claim 1 wherein a plurality of narrow grooves are formed at a suitable spacing in each of the upper and outer lateral sides of the lens rim, and at least some of the narrow grooves each have a channel communicating with a lens fitting groove, the narrow grooves and the communicating channels being filled with the soft material forming the hood member.

4. An eye protecting device as defined in claim 1 wherein each of the temples is formed with a bore vertically extending therethrough and filled with the soft material forming the hood member.

5. An eye protecting device as defined in claim 1 wherein at least one corner of the lens rim is formed in its inner face with a circular or rectangular groove shaped to have an enlarged interior space, and the circular or rectangular groove is filled with the soft material forming the hood member.

6. An eye protecting device as defined in claim 5 wherein the circular or rectangular groove has a channel communicating with a lens fitting groove, and the communicating channel is filled with the soft material forming the hood member.

7. An eye protecting device as defined in claim 1 wherein the lens rim forming rigid material has a higher melting point than the hood member forming soft material.

8. An eye protecting device as defined in claim 1 wherein each of the temples comprises an auxiliary temple and a main temple pivotably connected to the auxiliary temple with a hinge, and the hood member is provided in the form of a fin between the rim upper side and the auxiliary temple and between each rim outer lateral side and the auxiliary temple, the narrow groove being formed in the inner face of the auxiliary temple.

* * * * *